(12) United States Patent
Chou et al.

(10) Patent No.: US 11,859,237 B2
(45) Date of Patent: Jan. 2, 2024

(54) METHOD FOR SIZING DNA MOLECULE

(71) Applicant: Academia Sinica, Taipei (TW)

(72) Inventors: Chia-Fu Chou, Taipei (TW); Jia-Wei Yeh, Taipei (TW); Yii-Lih Lin, Taipei (TW)

(73) Assignee: ACADEMIA SINICA, Taipei (TW)

( * ) Notice: Subject to any disclaimer, the term of this patent is extended or adjusted under 35 U.S.C. 154(b) by 890 days.

(21) Appl. No.: 16/677,767

(22) Filed: Nov. 8, 2019

(65) Prior Publication Data

US 2020/0149088 A1    May 14, 2020

Related U.S. Application Data

(60) Provisional application No. 62/757,790, filed on Nov. 9, 2018.

(51) Int. Cl.
| | |
|---|---|
| *C12Q 1/68* | (2018.01) |
| *B01L 3/00* | (2006.01) |
| *G01N 15/14* | (2006.01) |
| *G01N 33/487* | (2006.01) |
| *G01N 15/10* | (2006.01) |
| *G01N 27/327* | (2006.01) |

(52) U.S. Cl.
CPC ............ *C12Q 1/68* (2013.01); *B01L 3/50273* (2013.01); *G01N 15/1404* (2013.01); *G01N 33/487* (2013.01); *B01L 2300/041* (2013.01); *B01L 2300/047* (2013.01); *B01L 2300/06* (2013.01); *B01L 2400/0406* (2013.01); *G01N 27/3272* (2013.01); *G01N 2015/1006* (2013.01); *G01N 2015/1493* (2013.01)

(58) Field of Classification Search
None
See application file for complete search history.

(56) References Cited

U.S. PATENT DOCUMENTS

| | | |
|---|---|---|
| 5,356,776 A | 10/1994 | Kambara et al. |
| 9,650,668 B2 | 5/2017 | Oliver et al. |

(Continued)

OTHER PUBLICATIONS

John J. Kasianowicz Eric Brandin Daniel Branton and David Deamer, Characterization of Individual Polynucleotide Molecules Using a Membrane Channel, Proceedings of the National Academy of Sciences, USA, vol. 93. pp. 13770-13773, Nov. 1996.

(Continued)

*Primary Examiner* — Matthew D Krcha
(74) *Attorney, Agent, or Firm* — BACON & THOMAS, PLLC

(57) ABSTRACT

A method for sizing a DNA molecule is disclosed, which comprises the following steps of: providing a DNA sizing device, comprising: a cover substrate; a substrate disposed on the cover substrate and comprising a first hole and a second hole; and a first slit-like channel disposed between the cover substrate and the substrate, wherein two ends of the first slit-like channel respectively connects to the first hole and the second hole; loading a sample comprising a DNA molecule to the first slit-like channel through the first hole, wherein the DNA molecule moves in a direction from the first hole to the second hole; detecting and recording an intensity and an area of a distribution of the DNA molecule; and analyzing the intensity and the area to obtain the size of a DNA molecule.

18 Claims, 6 Drawing Sheets

(56) References Cited

U.S. PATENT DOCUMENTS

2003/0231985 A1* 12/2003 Schleifer ................ B01L 3/508
422/400
2004/0009612 A1   1/2004 Zhao et al.
2014/0248183 A1* 9/2014 Oliver .............. G01N 33/48721
422/82.01

OTHER PUBLICATIONS

Dmitry Torchinsky and Yuval Ebenstein, Sizing femtogram amounts of dsDNA by single-molecule counting, Nucleic Acids Research, 2016, vol. 44, No. 2 e17.
Hou-Pu Chou, Charles Spence, Axel Scherer, Stephen R. Quake, Microfabricated devices for sizing DNA and sorting cells, SPIE vol. 3258.

* cited by examiner

METHOD FOR SIZING DNA MOLECULE

CROSS REFERENCE TO RELATED APPLICATION

This application claims the benefit of filing date of U.S. Provisional Application Ser. No. 62/757,790, entitled "Ultrafast size profiling of kilo-base to mega-base paired. DNA using optofluidic device" filed Nov. 9, 2018 under 35 USC § 119(e)(1).

BACKGROUND

1. Field

The present disclosure relates to a method for sizing a DNA molecule. More specifically, the present disclosure relates to a method for sizing a DNA molecule with Kilo to Mega base pairs.

2. Description of Related Art

Today, sizing of DNA is one of the crucial and routing processes for molecular biology research. This is especially necessary for processes in DNA fingerprinting, restriction mapping, epidemiologic genotyping, and the growing utility of next generation sequencing. Nevertheless, sizing large DNA fragments with length around 1,000~10,000,000 base pairs (kbp~10 Mbp) exists some challenges for various separation techniques.

Gel electrophoresis and Pulsed-field gel electrophoresis (PFGE) are the standard methods for separating small (<kbp) and large (>kbp) DNA by molecular weight, respectively. Although PFGE could separate DNA by using time-varying drive voltage to unfold the long DNA as it migrates, it takes 14 hours to separate 50 kbp DNA and is time consuming, and for DNA with 100's kbp, it may take days. Capillary Electrophoresis (CE) using polymer solution rather than slab gels, which allows higher applied voltages and concomitantly shorter separation times. However, CE still takes 1 hour to separate 50 kbp DNA.

Hence, it is desirable to provide a novel method which can size DNA molecules up to mega base pairs in a simple and fast way.

SUMMARY

The present disclosure relates to a method for sizing a DNA molecule, which can be used to size large DNA molecules (kilo to mega base pairs).

The method of the present disclosure comprises the following steps of providing a. DNA sizing device, comprising: a cover substrate; a substrate disposed on the cover substrate and comprising a first hole and a second hole; and a first slit-like channel disposed between the cover substrate and the substrate, wherein two ends of the first slit-like channel respectively connects to the first hole and the second hole; loading a sample comprising a DNA molecule to the first slit-like channel through the first hole, wherein the DNA molecule moves in a direction from the first hole to the second hole; detecting and recording an intensity and an area of a distribution of the DNA molecule; and analyzing the intensity and the area to obtain the size of the DNA molecule.

Pulsed-field gel electrophoresis (PFGE) and Capillary Electrophoresis (CE) are commercial methods for sizing large DNA molecules. PFGE can separate DNA molecule with mega base pairs, but this method is time consuming. CE uses the polymer solution rather than gels, so the separation time thereof is shorter than that of PFGE. However, the maximum size of the DNA molecules which can be separated by CE is only about 50 kilo base pairs. In the method of the present disclosure, the sample comprising the DNA molecule is a buffer solution, so the separation time of the method of the present disclosure can be greatly decreased. In addition, the size of the DNA molecule capable of being detected by the method of the present disclosure can be up to mega base pairs, so the application of the method of the present disclosure can be extended.

In the method of the present disclosure, the intensity and the area of the distribution of the DNA molecule can be analyzed by the following equation (I-1):

$$S = A \times (I - I_0)/m \quad (\text{I-1})$$

wherein, $I_0$ is a minimal value of a mean intensity of the intensity, m is a slope of a linear fitting of a plot displaying the intensity and the area, A is the area, I is the mean intensity, and S is an effective size of the DNA molecule. Herein, the effective size of the DNA molecule is proportional to the size of the DNA molecule.

In the method of the present disclosure, the DNA sizing device may further comprise a second slit-like channel disposed between the cover substrate and the substrate, wherein two ends of the second slit-like channel respectively connects to a third hole and a fourth hole of the substrate. Herein, the first slit-like channel can be substantially parallel to the second slit-like channel.

When the DNA sizing device comprises the first slit-like channel and the second slit-like channel, the sample comprising the DNA molecule and a DNA ladder comprising reference DNA molecules can be loaded into the DNA sizing device at the same time, and the DNA ladder can be used as a reference. Hence, in this case, the method of the present disclosure may further comprise the following steps of loading a DNA ladder comprising reference DNA molecules to the second slit-like channel through the third hole when loading the sample comprising the DNA molecule, wherein the reference DNA molecules move in a direction from the third hole to the fourth hole; detecting and recording intensities and areas of a distribution of the reference DNA molecules in the DNA ladder; and analyzing the intensities and the areas of the reference DNA molecules in the distribution of the DNA ladder.

When the sample comprising the DNA molecule and the DNA ladder comprising the reference DNA molecules are separated by the method of the present disclosure at the same time, the intensities and the areas of the distribution of the reference DNA molecules in the DNA ladder and the intensity and the area of the distribution of the DNA molecule in the sample can be respectively analyzed by the following equation (I-1):

$$S = A \times (I - I_0)/m \quad (\text{I-1})$$

wherein, $I_0$ is a minimal value of a mean intensity of the intensities of the reference DNA molecules or a minimal value of a mean intensity of the intensity of the DNA molecule, m is a slope of a linear fitting of a plot displaying the intensities and the areas of the reference DNA molecules or a slope of a linear fitting of a plot displaying the intensity and the area of the DNA molecule, A is the areas of the reference DNA molecules or the area of the DNA molecule, I is the mean intensity of the intensities of the reference DNA molecules or the mean intensity of the intensity of the DNA molecule, and S is an effective size of the reference DNA molecules or an effective size of the DNA molecule.

After Obtaining the effective sizes of the reference DNA molecules in the DNA ladder and the effective size of the DNA molecule in the sample, the effective size of the DNA molecule can be compared with the effective sizes of the reference DNA molecules. Because the effective size of the DNA molecule is proportional to the size of the DNA molecule, the size of the DNA molecule in the sample can be determined by comparing the effective size of the DNA molecule with the effective sizes of the reference DNA molecules, in which the sizes of the reference DNA molecules containing in the DNA ladder is known.

In the method of the present disclosure, the DNA sizing device may further comprise reservoirs disposed on the substrate and respectively connecting to the first hole and the second hole. In addition, the DNA sizing device may further comprise reservoirs disposed on the substrate and respectively connecting to the third hole and the fourth hole.

In the method of the present disclosure, the DNA molecule and the reference DNA molecules can be dissolved in a buffer solution (for example, the buffer solution used in PFGE such as a TAE buffer or a TBE buffer) or in water. Hence, the time for separating the DNA molecule and the reference DNA molecules can be greatly decreased.

In the method of the present disclosure, the force for moving the DNA molecule and the reference DNA molecules is not particularly limited, as long as the DNA molecule can move from the first hole to the second hole and the reference DNA molecules can move from the third hole to the fourth hole. For example, the DNA molecule and the reference DNA molecules can move by capillary flow, an electric filed or a flow field.

In the method of the present disclosure, the first slit-like channel and the second slit-like channel may respectively have a depth in a range from 100 nm to 10 µm, and preferably in a range from 500 nm to 3 µm. When the depths of the first slit-like channel and the second slit-like channel are outside the aforesaid range, the defocusing problem, which may influence the brightness of the DNA molecule and the reference DNA molecules, may be occurred. Thus, when the depths of the first slit-like channel and the second slit-like channel are within the aforesaid range, the intensities of the DNA molecule and the reference DNA molecules are basically resulted from the DNA molecule and the reference DNA molecules themselves.

In the method of the present disclosure, the lengths of the first slit-like channel and the second slit-like channel are not particularly limited. For example, the first slit-like channel and the second slit-like channel may respectively have a length in a range from 500 µm to 1 cm.

In the method of the present disclosure, the widths of the first slit-like channel and the second slit-like channel are not particularly limited. For example, the first slit-like channel and the second slit-like channel may respectively have a width in a range from 50 µm to 1 mm.

In the method of the present disclosure, the first slit-like channel and the second slit-like channel can weakly confine the DNA molecule in the sample and the reference DNA molecules in the DNA ladder in the vertical dimension by the depths of the first slit-like channel and the second slit-like channel, but not in lateral dimensions (i.e. the lengths or the widths of the first slit-like channel and the second slit-like channel). The DNA molecule in the sample and the reference DNA molecules in the DNA ladder are in an equilibrium state, and the DNA molecules in the sample and the reference DNA molecules in the DNA ladder are in sphere or pancake configurations; thus, the sizes of the DNA molecules in the sample and the reference DNA molecules the DNA ladder are proportional to the effective sizes thereof.

In the method of the present disclosure, the DNA molecule in the sample and the reference DNA molecules in the DNA ladder can be respectively fluorescently labeled. Herein, the dye for labeling the DNA molecule and the reference DNA molecules is not particularly limited. When the DNA molecule and the reference DNA molecules are fluorescently labeled, the distributions of the DNA molecule and the reference DNA molecules can be detected by a fluorescence microscope and recorded by a camera such as a CCD or CMOS camera.

In the method of the present disclosure, the substrate of the DNA sizing device can be a glass substrate, a silica substrate, a polymethylmethacrylate (PMMA) substrate, or a plastic substrate, but the present disclosure is not limited thereto. In one aspect of the present disclosure, the substrate is a fused silica substrate.

In the method of the present disclosure, the cover substrate of the DNA sizing device can be a borosilicate glass substrate, but the present disclosure is not limited thereto.

In the method of the present disclosure, the cover substrate can be attached on the substrate via thermal bonding without any coating. Alternatively, the cover substrate can be a glass coated with a polymer such as polysilsesquioxane, and the cover substrate can be attached on the substrate via a polymer bonding technique. However, the present disclosure is not limited thereto.

Other novel features of the disclosure will become more apparent from the following detailed description when taken in conjunction with the accompanying drawings.

DETAILED DESCRIPTION OF EMBODIMENT

Figure 1A:
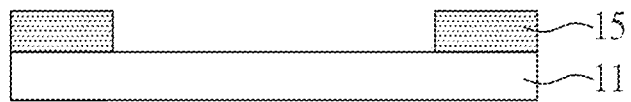
FIG. 1A to FIG. 1E are cross-sectional views showing a process for manufacturing a DNA sizing device according to an embodiment of the present disclosure.

The following embodiments when read with the accompanying drawings are made to clearly exhibit the above-mentioned and other technical contents, features and/or effects of the present disclosure. Through the exposition by means of the specific embodiments, people would further understand the technical means and effects the present disclosure adopts to achieve the above-indicated Objectives. Moreover, as the contents disclosed herein should be readily understood and can be implemented by a person skilled in the art, all equivalent changes or modifications which do not depart from the concept of the present disclosure should be encompassed by the appended claims.

Furthermore, the ordinals recited in the specification and the claims such as "first", "second" and so on are intended only to describe the elements claimed and imply or represent neither that the claimed elements have any proceeding ordinals, nor that sequence between one claimed element and another claimed element or between steps of a manufacturing method. The use of these ordinals is merely to differentiate one claimed element having a certain designation from another claimed element having the same designation.

Furthermore, the terms recited in the specification and the claims such as "above", "over", or "on" are intended not only directly contact with the other element, but also intended indirectly contact with the other element. Similarly, the terms recited in the specification and the claims such as "below", or "under" are intended not only directly contact with the other element but also intended indirectly contact with the other element.

Furthermore, when a value is in a range from a first value to a second value, the value can be the first value, the second value, or another value between the first value and the second value.

Sample Preparation

The sample containing fragments of two lengths (3 kbp and 6 kbp) is a plasmid DNA digests with the restriction enzyme.

The sample, the DNA ladder (Lambda DNA-HindIII Digest, NEB) and the λ-DNA Mono Cut ladder were stained with YOYO-1 fluorescent dye (Invitrogen) at 1:5 dye/base pair ratio. The sample, the DNA ladder (Lambda DNA-HindIII Digest, NEB) and the λ-DNA Mono Cut ladder were initially prepared at 0.1 μg/ml in 0.5×TBE buffer (Sigma) containing 2.5% (w/w) poly(n-vinylpyrrolidone) (PVP, Sigma, used to suppress electro-osmotic flow), 30% (w/v) sucrose (J. T. Baker), 50 μg/mL and 10 (w/v) glucose Sigma) used to increase solution viscosity and to slow down the dynamics of DNA molecules for easy imaging. The buffer viscosity was 4.1 cP measured by a viscometer (Toki Sangyo). An oxygen scavenging system containing 0.5% (v/v) 3-mercaptoethanol (BME, Sigma), 50 μg/mL glucose oxidase Sigma), and 10 μg/mL catalase (Roche) was used to reduce photobleaching.

Microscopy and Image Analysis

DNA molecules were Observed with a fluorescence microscopy system consisting of an inverted microscope (Leica DMI6000), 100× oil-immersion or 40× lens (Leica, N.A. 1.35), and EMCCD camera (IXon-888, Andor Technologies' with an equivalent pixel resolution of 130 nm. Images were captured at a rate of 1 frames/sec. DNA movement was analyzed from the CCD images by MATLAB (The Mathworks, Natick, MA).

Preparation of DNA Sizing Device

FIG. 1A to FIG. 1E are cross-sectional views showing a process for manufacturing a DNA sizing device according to an embodiment of the present disclosure.

Figure 1B:
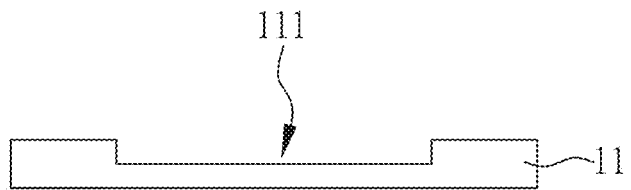
Figure 1C:
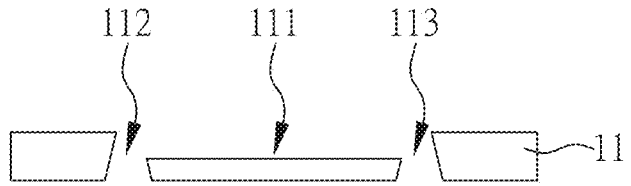
Figure 1D:
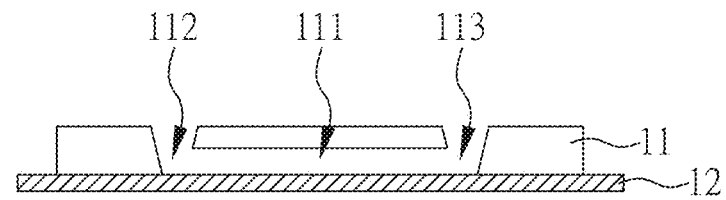
Figure 1E:
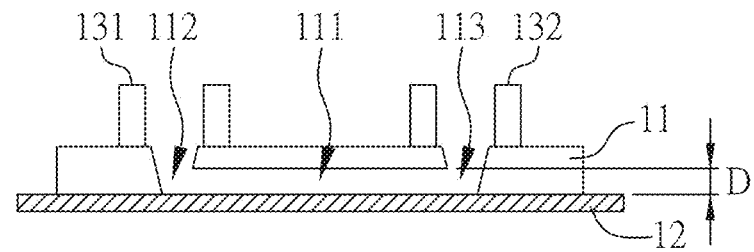

As shown in FIG. 1A, a substrate 11 was provided, which was a fused silica substrate. The size of the substrate 11 was 1.4 cm square and 500 μm thick. A mask 15 made of a photoresist was disposed on the substrate 11. As shown in FIG. 1B, a first slit-like channel 111 and a second slit-like channel (not shown in the figure) were formed by standard photolithography followed by the etching process. The first slit-like channel 111 and the second slit-like channel (not shown in the figure) were etched by inductively coupled plasma (ICP) with a $CHF_3/CF_4/Ar/O_2$ mixture at bias/RF power 700/300W for 1 min. As shown in FIG. 1C, a first hole 112, a second hole 113, a third hole (not shown in the figure) and a fourth hole (not shown in the figure) were formed by sandblaster drilling through a stainless steel mask from the backside of the device with the feature side protected by photoresist, which was later removed by acetone and cleaned. The first hole 112 and the second hole 113 connected to the first slit-like channel 111, and the third hole (not shown in the figure) and the fourth hole (not shown in the figure) connected to the second slit-like channel (not shown in the figure). As shown in FIG. 1D, the first slit-like channel 111 and the second slit-like channel (not shown in the figure) were simultaneously bonded by a polysilsesquioxane (PSQ) coated cover substrate 12 via an oxygen plasma surface treatment, wherein the cover substrate 12 was a borosilicate glass substrate. As shown in FIG. 1E, reservoirs 131, 132 were attached on the substrate 11 by fast-curing glue and respectively connecting to the first hole 112, the second hole 113, the third hole (not shown in the figure) and the fourth hole (not shown in the figure). Thus, the DNA sizing device of the present embodiment was obtained.

Figure 2:
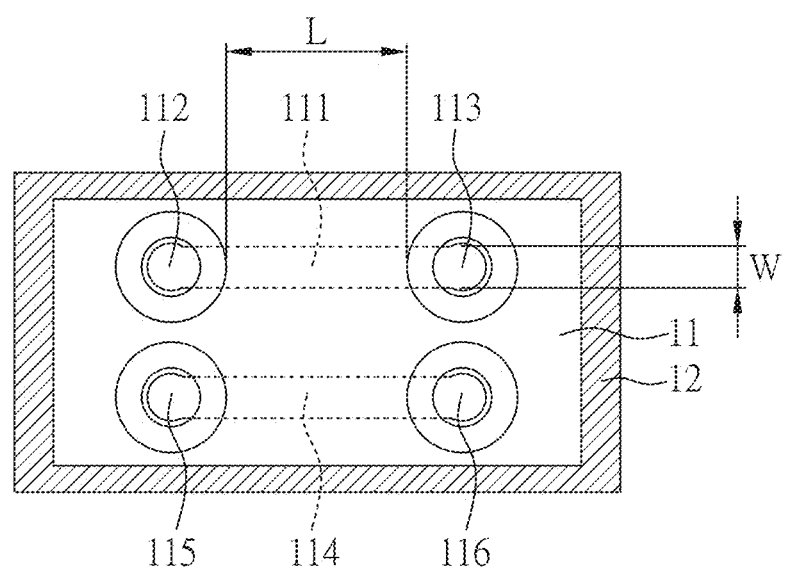
FIG. 2 is a top view of a DNA sizing device according to an embodiment of the present disclosure.

FIG. 2 is a top view of a DNA sizing device of the present embodiment. As shown in FIG. 1E and FIG. 2, the DNA sizing device comprises: a cover substrate 12; a substrate 11 disposed on the cover substrate 12 and comprising a first hole 112, a second hole 113, a third hole 115 and a fourth hole 116; and a first slit-like channel 111 and a second slit-like channel 114 disposed between the cover substrate 12 and the substrate 11, wherein two ends of the first slit-like channel 111 respectively connects to the first hole 112 and the second hole 113, and two ends of the second slit-like channel 114 respectively connects to the third hole 115 and the fourth hole 116. In addition, the DNA sizing device of the present embodiment further comprises: reservoirs 131, 132 disposed on the substrate 11 and respectively connecting to the first hole 112 and the second hole 113. Even not shown in the figure, other reservoirs are also disposed on the substrate 11 and respectively connects to the third hole 115 and the fourth hole 116.

In the present embodiment, the first slit-like channel 111 and the second slit-like channel 114 respectively have a depth D of 500 nm or 3 μm, a width W of 100 μm and a length L of 100 μm. In addition, the first slit-like channel 111 is substantially parallel to the second slit-like channel 114.

Test Example 1

The DNA sizing device shown in FIG. 1E and FIG. 2 is used in the present test example. Reference DNA molecules in a DNA ladder (Lambda DNA-HindIII Digest, NEB) were fluorescently labeled with intercalating dye YOYO-1. The DNA ladder was loaded in the reservoir 131 connecting to the first hole 112 and driven into the first slit-like channel 111 by capillary flow. The depth D of the first slit-like channel 111 was 500 nm. Then, the distribution of the reference DNA molecules in the DNA ladder was detected by fluorescence microscope with 100× oil-immersion or 40× objectives (numerical aperture: 1.35 and 0.6) and recorded by a CCD camera (Andor). Later, we processed the images by using software (Matlab, The MathWorks, Natick MA) developed specifically for the present disclosure, finally reporting of order $10^5$ individual DNA molecules for statistical analysis by using Python 3.

Figure 3:
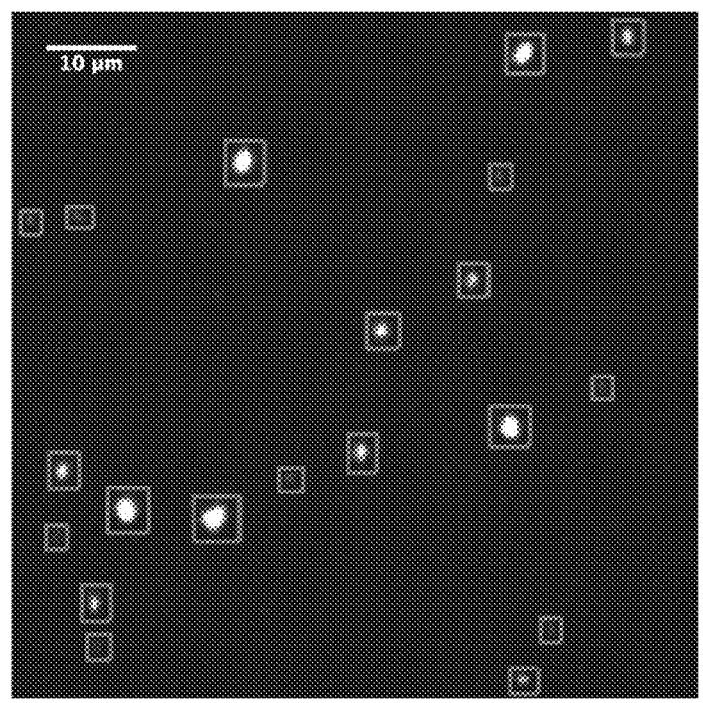
FIG. 3 is an image of a distribution of reference DNA molecules in a DNA ladder according to Test example 1 of the present disclosure.

The image of the distribution of the reference DNA molecules in the DNA ladder is shown in FIG. 3, in which the rectangles indicate the tracking analysis of a single field of view from the DNA ladder.

Figure 4:
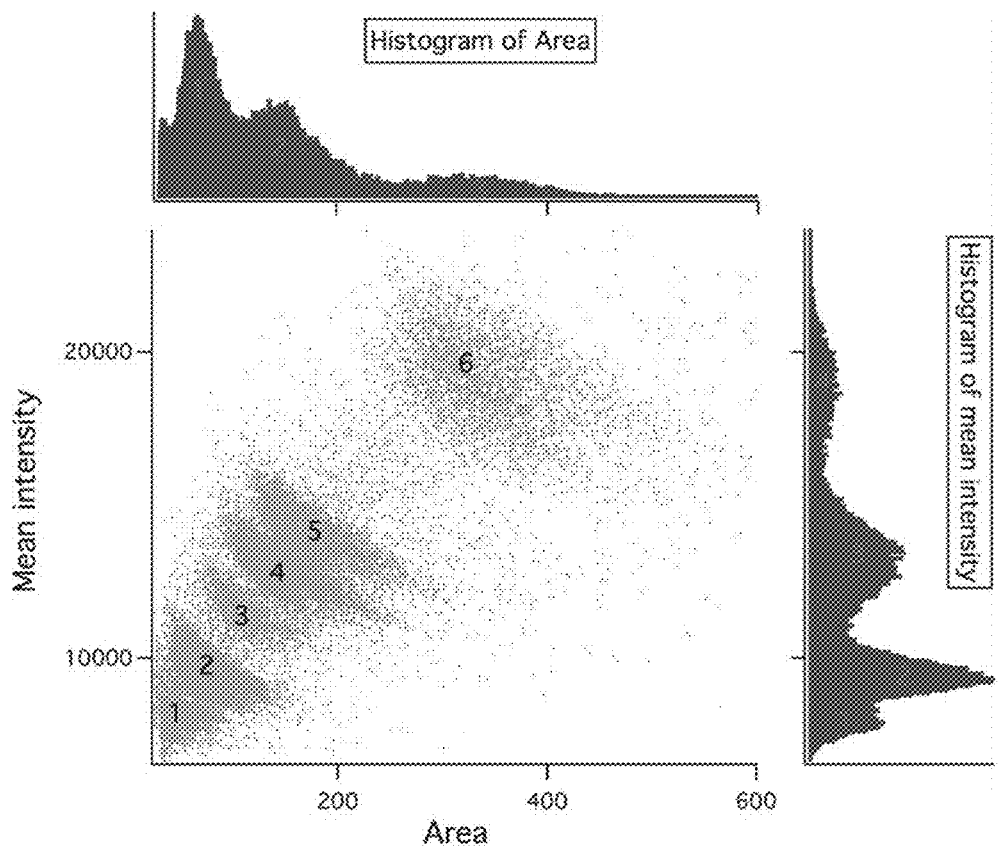
FIG. 4 is a typical scatter plot displaying values for molecular area and mean intensity according to Test example 1 of the present disclosure.

After image processing, we can extract features such as: mean intensity (I, total intensity per unit area), projected area (A), major axis length ($R_g$), and minima axis length. The most two important features are mean intensity and projected area. However, the resulting distribution of mean intensity and projected area contains 3 and 4 peaks corresponding to the 6 DNA populations in the sample. Surprisingly, the mean intensity and area coordinate scatter plot depicts a better resulting distribution than itself along, which contains the same number of peaks of the sample. The DNA size are ranging from 80 nm to 810 nm (for the 1 kb~48 kb molecules) based on the standard Flory radius $R_g=(\pi b w a^{3/4})^{1/5} N^{3/5}$, where b is the persistence length, w is the width, a is the monomer size, and N is the total number of monomers. The first slit-like channel 111 shown in FIG. 1E and FIG. 2 are weakly confining the DNA molecules in the vertical dimensions ($R_g \leq D$ shown in FIG. 1E) but not in the lateral dimensions ($R_g \ll W$ shown in FIG. 2). Thus, we postulate that in an equilibrium state, the DNA molecules are in sphere or pancake configurations. For the behavior of polymer in a steady fluid flow in a capillary slit (for example, the first slit-like channel 111 shown in FIG. 1E and FIG. 2), a parabolic velocity gradient along the y direction may stretch and orient polymers far from equilibrium. Whenever a DNA polymer elongates, the conformational of a polymer sphere in response to a larger projected area and lower fraction in y direction which lead a smaller mean intensity, as shown in FIG. 4, Remarkably, though the most separation methods base on molecular mobility difference due to the factors such as molecular weight, charge, and the friction of buffer and surface, the only factor we consider is by their size features.

Figure 5:
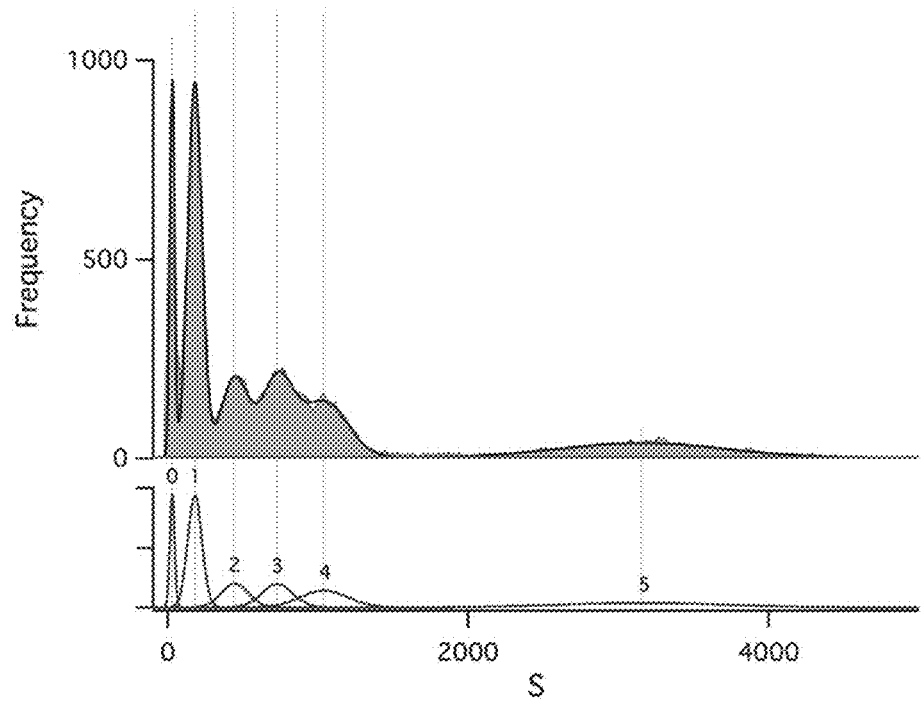
FIG. 5 is a histogram showing the effective size distribution of reference DNA molecules in a DNA ladder according to Test example 1 of the present disclosure.
Figure 6:
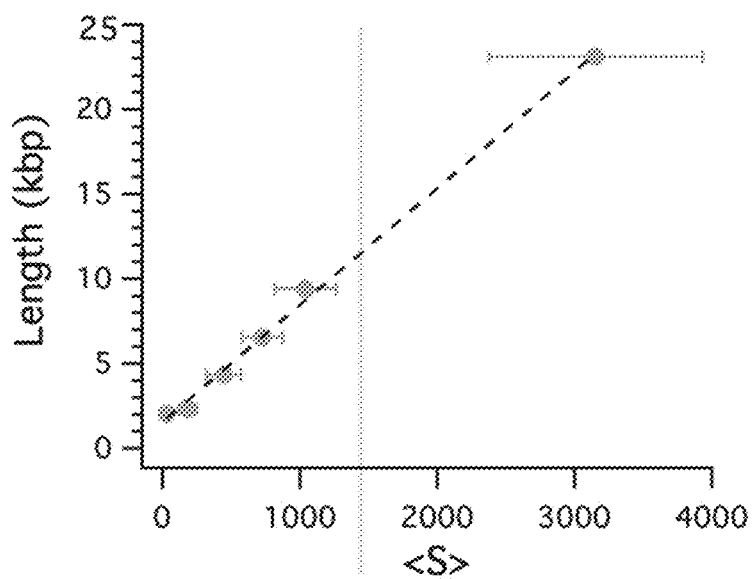
FIG. 6 is a plot showing the lengths of reference DNA molecules in a DNA ladder verse the centers of the fitted peaks with a linear fitting according to Test example 1 of the present disclosure.

In order to reduce the dimension of the data and construct a proper characteristic of DNA, we could use Principle Component Analysis (PCA) for characteristic the new feature of molecule. We preprocessed the data by standardization, and following by PCA transformation. In FIG. 5 and FIG. 6, we represent the histogram of the data collapse on the first principle component. We obtain 6 distinct peaks corresponding to the 6 DNA populations in the sample (number of molecules: $4\lambda 10^4$). We call the new feature to be an effective size (S). We could also obtain the distinguished size (S) spectrum by simply multiply the A and (I–$I_0$), where $I_0$ is the minimal values of the mean intensity and m is a slop slope of a linear fitting of the plot shown in FIG. 4.

$$S = A \times (I - I_0)/m \tag{I-1}$$

We fit the curve with multi-Gaussian function and extract the mean effective size ($<S_i>$, $i \in [0, 5]$) and the standard deviation for different populations, as shown in FIG. 5, in which the curves are fitted by multi-Gaussian for each population. We plot the mean effective size corresponding to the expected length of the DNA populations, as shown in FIG. 6 which exhibits linear dependency with $R^2$=0.9899. The relationship between them is linear and the average resolution between two nearby populations is 1.36. This linear ruler could provide us an advantage scheme for predicting and sizing an unknown sample.

Base on the reference data, we can predict the sample size whether it is in the same classification or not. To identify the size of DNA molecule within the same populations of the ladder, we can use K-nearest neighborhood classification (KNN), a branch of supervised learning for the purpose. We train the first 70% of the data, and test the classification result from the rest of them. We choose a best K-value by Elbow method. The following Table 1 shows the classification report, which indicates the model can propose a good classification result.

TABLE 1

|  | precision | recall | f1-score | support |
| --- | --- | --- | --- | --- |
| 0 | 0.96 | 0.95 | 0.96 | 1387 |
| 1 | 0.98 | 0.98 | 0.98 | 3903 |
| 2 | 0.95 | 0.93 | 0.94 | 856 |
| 3 | 0.94 | 0.95 | 0.95 | 1546 |
| 4 | 0.98 | 0.97 | 0.97 | 2467 |
| 5 | 1.00 | 0.99 | 0.99 | 1728 |
| avg/total | 0.97 | 0.97 | 0.97 | 11887 |

Test Example 2

To promote quantitative sizing of an unknown sample, a sample containing DNA molecules and the DNA ladder (Lambda DNA-HindIII Digest, NEB) comprising reference DNA molecules as a standard were separately loaded into two parallel slit-like channels (i.e. the first slit-like channel 111 and the second slit-like channel 114 shown in FIG. 2). The sample contained fragments of two lengths (3 kbp and 6 kbp) obtained from a plasmid DNA digested with a restriction enzyme. The sample containing DNA molecules was loaded into the first slit-like channel 111, and the DNA molecules moved in a direction form the first hole 112 to the second hole 113. The DNA ladder was loaded into the second slit-like channel 114, and the reference DNA molecules contained in the DNA ladder moved in a direction from the third hole 115 to the fourth hole 116. Then, the images of the distribution of the sample and the DNA ladder were detected and recorded. After performing the analysis the same as that described in Text example 1, a histogram of the sample and the DNA ladder was plotted.

Figure 7:
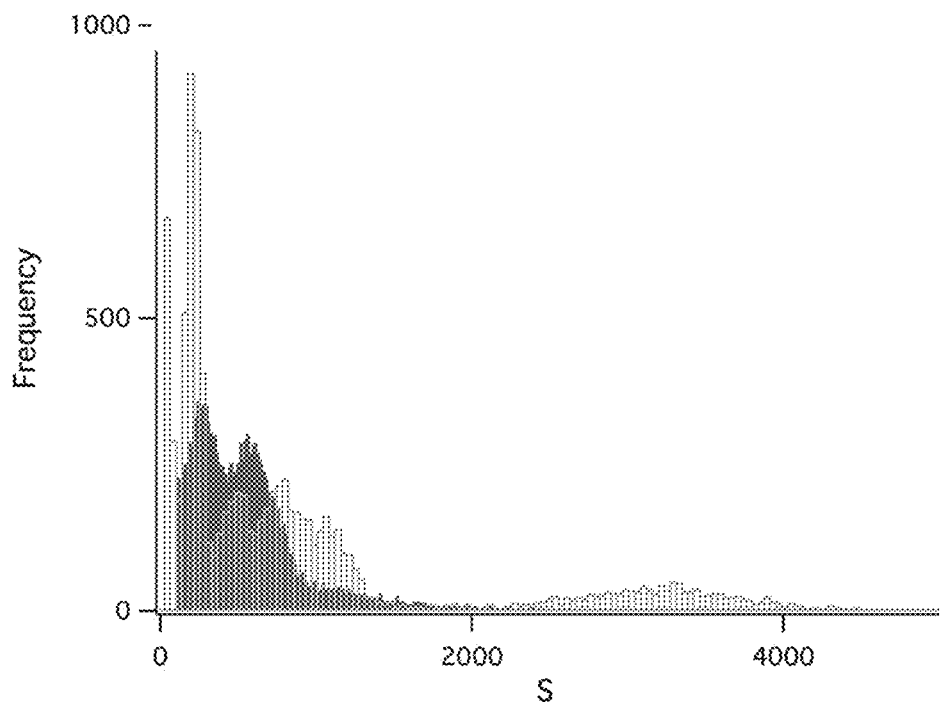
FIG. 7 is a histogram showing the effective size distribution of a sample containing DNA molecules and a DNA ladder containing reference DNA molecules according to Test example 2 of the present disclosure.
Figure 8:
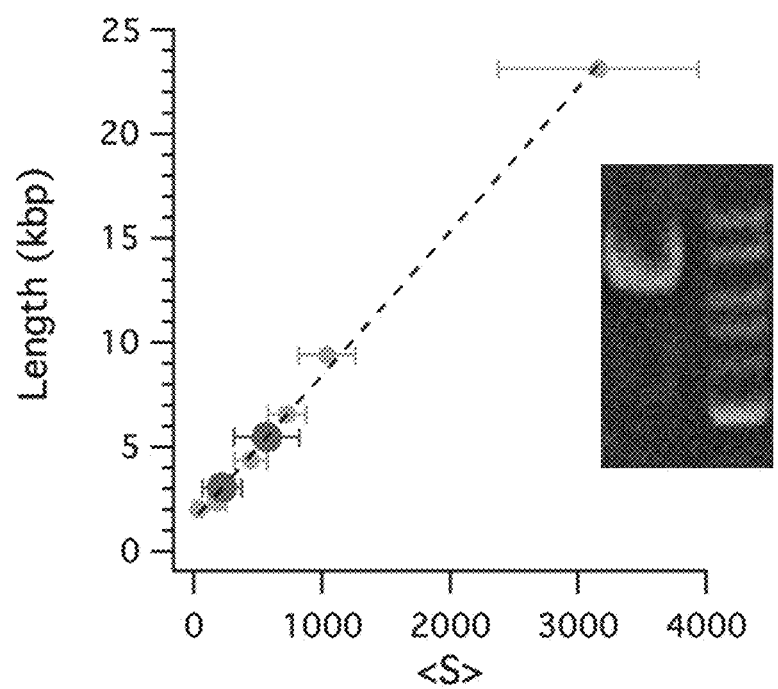
FIG. 8 is a plot showing the expected lengths of DNA molecules in a sample and the lengths of reference DNA molecules in a DNA ladder verse the centers of the fitted peaks with a linear fitting according to Test example 2 of the present disclosure.

FIG. 7 is a histogram showing the effective size distributions of the sample containing the DNA molecules and the DNA ladder containing the reference DNA molecules, in which the rectangles with darker color refer to the DNA molecules contained in the sample, the rectangles with brighter color refer to the reference DNA molecules contained in the DNA ladder, and the averaged resolution between each two brighter color peaks is 1.37. FIG. 8 is a plot showing the expected lengths of the DNA molecules in the sample and the reference DNA molecules in the DNA ladder verse the centers of the fitted peaks with a linear fitting, wherein the small dots with brighter color refer to the fitted effective sizes versus the expected ladder lengths of the reference DNA molecules in the DNA ladder, the dash line corresponds to the linear fit for conversion of intensity to length in kilo base pairs, and the large dots with darker color represent the two detected points in the sample.

As shown in FIG. 8, when the locations of the two detected points of the sample (i.e. the effective sizes of the DNA molecules in the sample) are compared with the locations of the points of the DNA ladder (i.e. the effective sizes of the reference DNA molecules in the DNA ladder), we can see that the sample data are located in a reference ladder (1-25 kbp). By using linear regression, we can measure the sample DNA length of 2,784 bp and 5,432 bp, which is close to the expected length (2430 bp & 6743 bp).

Test Example 3

In order to validate the power of this technique, we demonstrate the linear dependency of various standard reference DNA ladder ranging from kbp to Mbp. Herein, the method used in the present test example is similar to the method used in Text example 1, except that following differences.

The DNA ladder used herein was λ-DNA Mono Cut ladder.

Figure 9:
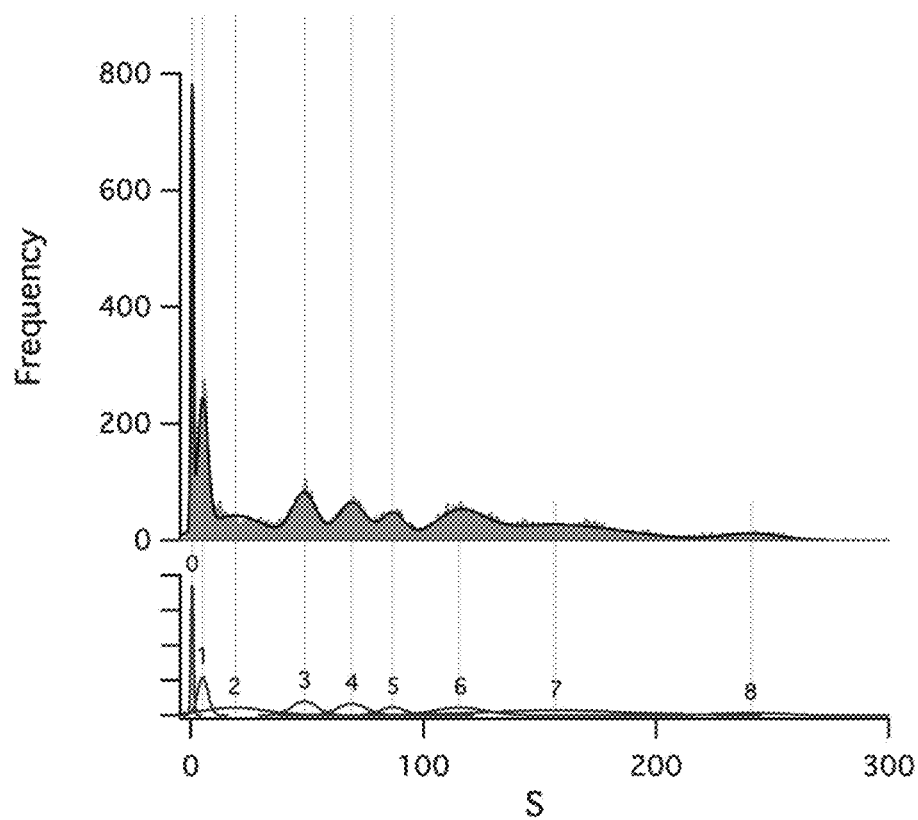
FIG. 9 is a histogram showing the effective size distribution of reference DNA molecules in a DNA ladder according to Test example 3 of the present disclosure.
Figure 10:
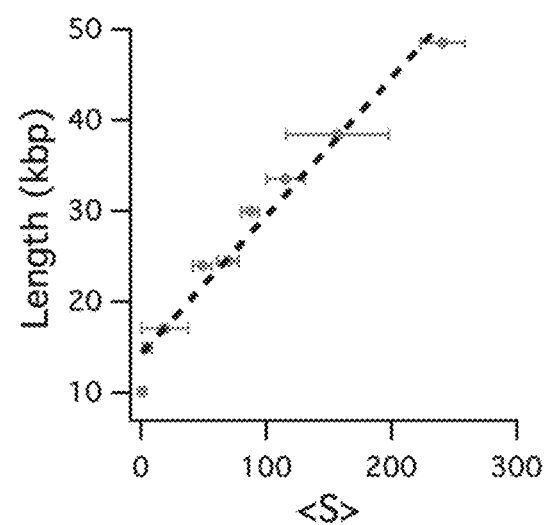
FIG. 10 is a plot showing the lengths of reference DNA molecules in a DNA ladder verse the centers of the fitted peaks with a linear fitting according to Test example 3 of the present disclosure.

After performing the analysis the same as that described in Text example 1, the results can be shown in FIG. 9 and FIG. 10. FIG. 9 is a histogram of an effective size of λ-DNA Mono Cut ladder, in which the curves are fitted by multi-Gaussian for each population. FIG. 10 is a plot showing expected length versus mean effective size (dots), which exhibits linear dependency with $R^2$=0.97.

In conclusion, the present disclosure provides a simple method with the ability to size the DNA molecules in the sample in minutes. Unlike conventional PFGE which takes 14 hours to separate 50 kbp DNA ladders, or capillary electrophoresis which takes 1 hour, the DNA sizing device of the present disclosure enables faster detection and lower sample volume and number of molecules. In addition, the method of the present disclosure provides unique opportunities for the sizing of large macromolecules, such as genomic DNA or chromosomes.

Although the present disclosure has been explained in relation to its embodiment, it is to be understood that many other possible modifications and variations can be made without departing from the spirit and scope of the disclosure as hereinafter claimed.

What is claimed is:

1. A method for sizing a DNA molecule, comprising the following steps of:
   providing a DNA sizing device, comprising:
      a cover substrate;
      a substrate disposed on the cover substrate and comprising a first hole and a second hole; and
      a first slit-like channel disposed between the cover substrate and the substrate, wherein two ends of the first slit-like channel respectively connects to the first hole and the second hole;
   loading a sample comprising a DNA molecule to the first slit-like channel through the first hole, wherein the DNA molecule moves in a direction from the first hole to the second hole;
   taking a first image related to a distribution of the DNA molecule;
   detecting and recording first intensity values of the DNA molecule and a first area of distribution which corresponds to an area of all the detected first intensity values of the DNA molecule which is detected from the first image; and
   analyzing the first intensity values and the first area to obtain a size of the DNA molecule.

2. The method of claim 1, wherein the first intensity values and the first area are analyzed by the following equation (I-1):

$$S = A \times (I - I_0)/m \quad (I-1)$$

wherein, $I_0$ is a value of a mean intensity of the first image, m is a slope of a linear fitting of a plot displaying the first intensity values and the first area, A is the first area, I is the mean intensity of the first intensity values, and S is an effective size of the DNA molecule.

3. The method of claim 2, wherein the effective size of the DNA molecule is proportional to the size of the DNA molecule.

4. The method of claim 1, wherein the DNA sizing device further comprises a second slit-like channel disposed between the cover substrate and the substrate, wherein two ends of the second slit like channel respectively connects to a third hole and a fourth hole of the substrate, and the method further comprises the following steps of:
   loading a DNA ladder comprising reference DNA molecules to the second slit-like channel through the third hole when loading the sample comprising the DNA molecule, wherein the reference DNA molecules move in a direction from the third hole to the fourth hole;
   taking a second image related to a distribution of the reference DNA molecules;
   detecting and recording second intensity values of the reference DNA molecules and a second area of distribution which corresponds to an area of all the detected second intensity values of the reference DNA molecule which is detected from the second image; and
   analyzing the second intensity values and the second area.

5. The method of claim 4, wherein the first intensity values, the first area, the second intensity values and the second area are respectively analyzed by the following equation (I-1):

$$S = A \times (I - I_0)/m \quad (I-1)$$

wherein, $I_0$ is a value of a mean intensity of the first image or a value of a mean intensity of the second image, m is a slope of a linear fitting of a plot displaying the second intensity values and the second area or a slope of a linear fitting of a plot displaying the first intensity values and the first area, A is the first area or the second, I is the mean intensity of the first intensity values or the mean intensity the second intensity values, and S is an effective size of the reference DNA molecules or an effective size of the DNA molecule.

6. The method of claim 5, further comprising the following step of:
   comparing the effective size of the DNA molecule with the effective sizes of the reference DNA molecules to obtain the size of the DNA molecule.

7. The method of claim 4, wherein the first slit-like channel is substantially parallel to the second slit-like channel.

8. The method of claim 4, wherein the DNA molecule and the reference DNA molecules move by capillary flow, an electric field or a flow field.

9. The method of claim 4, wherein the first slit-like channel and the second slit-like channel respectively have a depth in a range from 100 nm to 10 μm.

10. The method of claim 4, wherein the first slit-like channel and the second slit-like channel respectively have a length in a range from 500 μm to 1 cm.

11. The method of claim 4, wherein the first slit-like channel and the second slit-like channel respectively have a width in a range from 50 μm to 1 mm.

12. The method of claim 4, wherein the DNA molecule and the reference DNA molecules are respectively fluorescently labeled.

13. The method of claim 1, wherein the DNA sizing device further comprises reservoirs disposed on the substrate and respectively connecting to the first hole and the second hole.

14. The method of claim 1, wherein the DNA molecule moves by a capillary flow, an electric field or a flow field.

15. The method of claim 1, wherein the first slit-like channel has a depth in a range from 100 nm to 10 μm.

16. The method of claim 1, wherein the first slit-like channel has a length in a range from 500 μm to 1 cm.

17. The method of claim 1, wherein the first slit-like channel has a width in a range from 50 μm to 1 mm.

18. The method of claim 1, wherein the DNA molecule is fluorescently labeled.

* * * * *